US00PP33305P2

(12) United States Plant Patent
Olesen

(10) Patent No.: US PP33,305 P2
(45) Date of Patent: Aug. 3, 2021

(54) ***ROSA* PLANT NAMED 'POULCAS056'**

(50) Latin Name: *Rosa hybrida*
Varietal Denomination: Poulcas056

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/974,001

(22) Filed: Sep. 3, 2020

(51) Int. Cl.
*A01H 5/02* (2018.01)
*A01H 6/74* (2018.01)

(52) U.S. Cl.
USPC ..... Plt./145
CPC ..... *A01H 6/749* (2018.05)

(58) Field of Classification Search
USPC ..... Plt./145
CPC ..... A01H 5/0222
See application file for complete search history.

(56) References Cited

PUBLICATIONS https://www.poulsenroser.dk/en/roses/ShowProduct/29756; Dec. 5, 2020; 2 pages.*

* cited by examiner

*Primary Examiner* — Kent L Bell

(57) ABSTRACT

A new garden rose plant of the Floribunda class which has abundant, yellow flowers and attractive foliage. This new and distinct variety has shown to be uniform and stable in the resulting generations from asexual propagation.

3 Drawing Sheets

Botanical designation: *Rosa hybrida.*
Variety denomination: 'Poulcas056'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2006 and the resulting seeds were planted in a controlled environment in Fredensborg, Denmark. The new variety, named 'Poulcas056', originated as a single seedling from the stated cross.

The new variety may be distinguished from its male pollen parent and female seed parent primarily by the following characteristics. The male pollen parent plant has yellow flowers and grows to a height of 75 to 90 cm while the new variety has yellow flowers and grows to a height of 100 to 115 cm. The female seed parent plant has light yellow to near white petals flowers while the new variety has yellow flower petals.

The objective of the hybridization of this rose variety was to create a new and distinct variety with unique qualities, such as:

1. Uniform and abundant yellow flowers;
2. Vigorous, but compact growth when propagated on its own roots;
3. Exceptional disease resistance.

This combination of qualities is not present in previously available commercial cultivars of this type, known to the inventor, and distinguish 'Poulcas056' from all other varieties of which we are aware.

As part of the rose development program, Mogens N. Olesen germinated the seeds from the aforementioned hybridization during winter of 2006 and conducted evaluations on the resulting seedlings in a controlled environment in Fredensborg, Denmark. 'Poulcas056' was selected in the spring of 2007 by the inventor as a single plant from the progeny of the aforementioned hybridization.

Asexual reproduction of 'Poulcas056' by rooted cuttings was first done by Mogens N. Olesen in the nursery in Fredensborg, Denmark in July, 2007. This initial and other subsequent asexual propagations conducted in controlled environments have demonstrated that the characteristics of 'Poulcas056' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcas056'.

Specifically illustrated in FIG. 1 of the drawings are open flowers, petals and sepals detached, showing reproductive flower parts.

Figure 1:
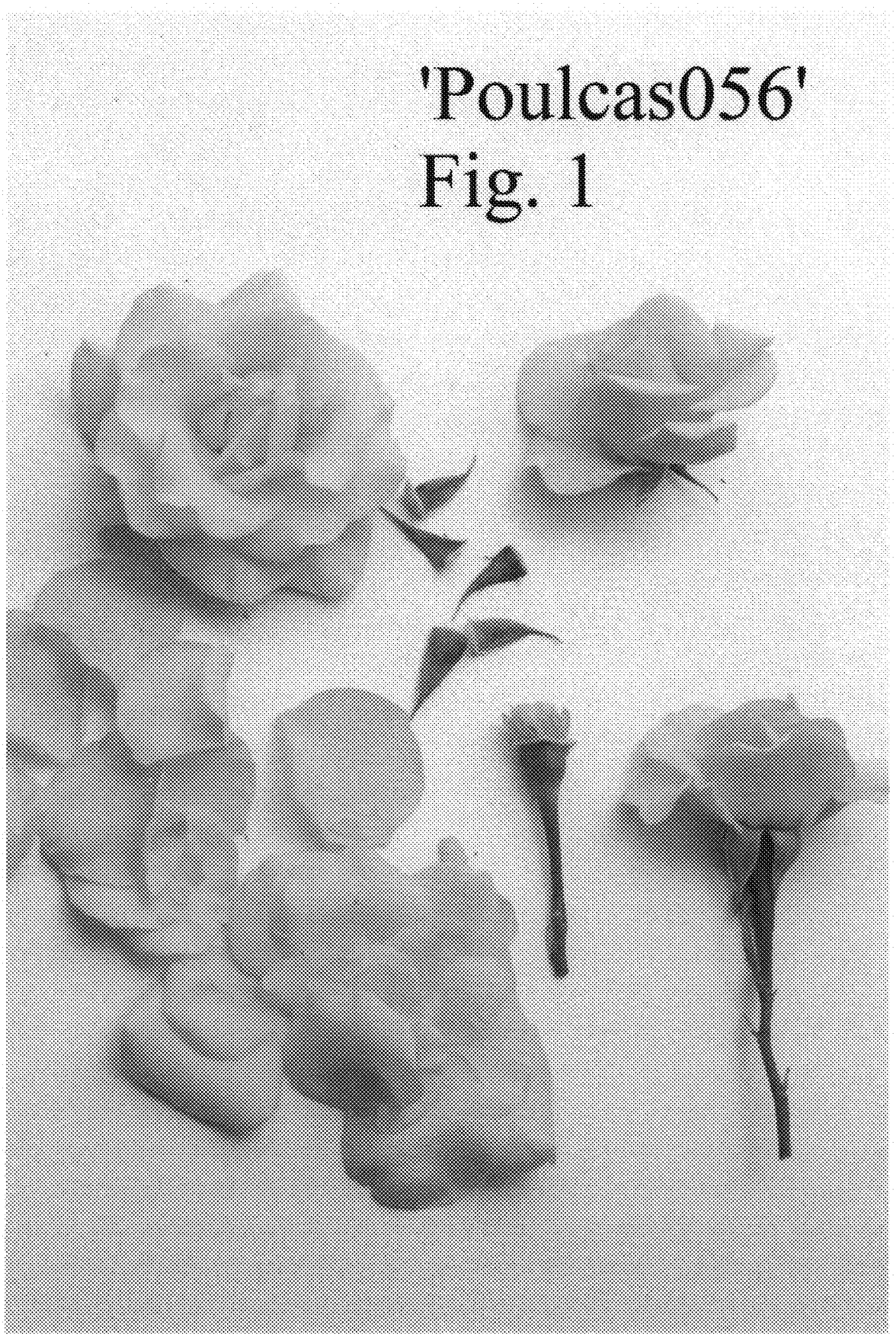
Figure 2:
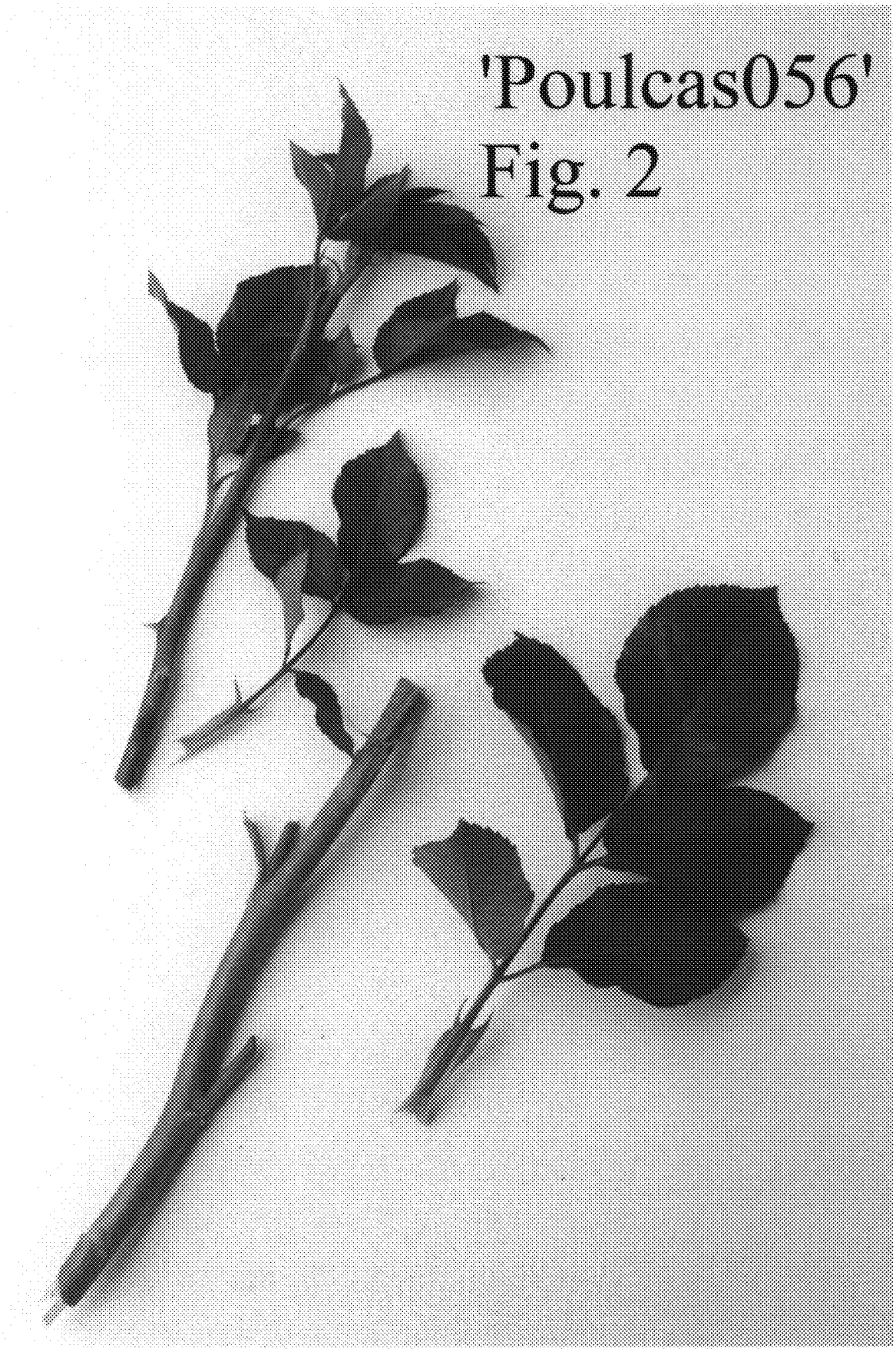

Specifically illustrated in FIG. 2 of the drawings are mature and juvenile leaves and bare stem.

Figure 3:
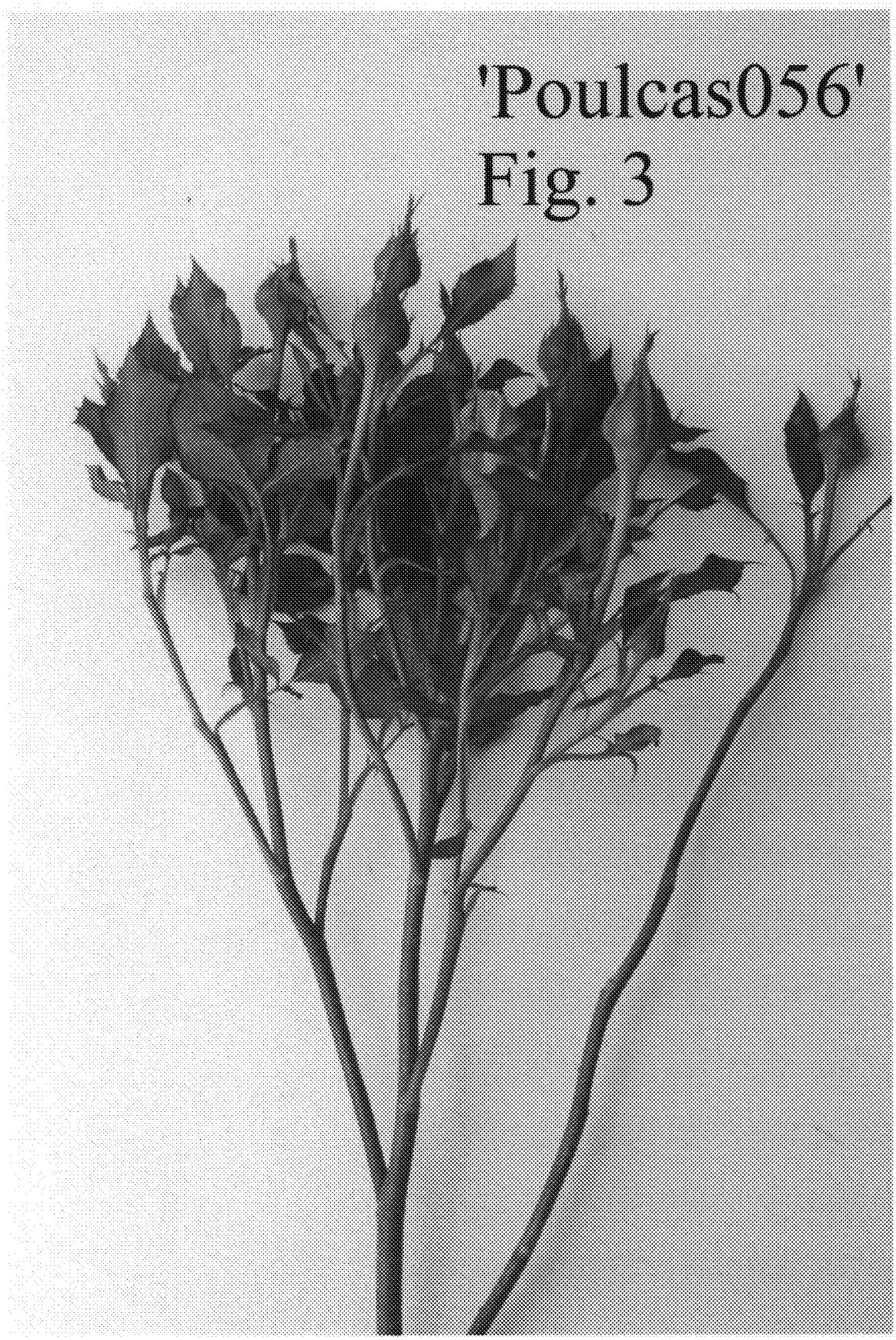

Specifically illustrated in FIG. 3 of the drawings is a cluster of flower buds on the branch. Plants shown are 2 years of age.

DETAILED DESCRIPTION OF THE VARIETY

The following is a description of 'Poulcas056', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulcas039', U.S. Plant Pat. No. 24,277 are compared to 'Poulcas056' in Chart 1.

CHART 1

| | 'Poulcas056' | 'Poulcas039' |
|---|---|---|
| Petal Count | 35 | 50 |
| Flower Diameter | 110 mm | 75 mm |
| General Tonality of Flower Color | Yellow Group 9B | Yellow Group 5D to Yellow 9C |

FLOWER AND FLOWER BUD

Blooming habit: Continuous.

Flower bud:

*Size*.—Upon opening, 32 mm in length from base of receptacle to end of bud. Bud diameter is 19 mm.

*Bud form*.—Ovoid.

*Bud color*.—As sepals divide petals are Yellow Group 10A.

*Sepal inner surface*.—Color: Yellow-Green Group 145C. Surface: Lightly pubescent.

*Sepal outer surface*.—Color: Yellow-Green Group 144A. Texture: Slightly rough with stipitate glands.

*Sepal shape*.—Apex: Cirrhose. Base: Flat at union with receptacle. Shape: Lanceolate.

*Sepal margin*.—Margins have weak foliaceous appendages on three of the five sepals.

*Sepal size*.—35 mm long, 12 mm wide.

*Receptacle*.—Texture: Smooth. Size: 10 mm in height, 11 mm wide. Color: Yellow-Green Group 144A. Shape: Funnel.

*Pedicel*.—Surface: Smooth. Length: 40 mm. Diameter: 3 mm on average. Color: Yellow-Green Group 144C with intonations of Greyed-Red Group 179B. Strength: Strong.

*Peduncle*.—Length: 5 to 20 cm. Diameter: About 4 mm. Color: Yellow-Green Group 144A with intonations of Greyed-Red Group 180B. Texture: Smooth.

Flower bud development: Flower buds are borne in clusters of 3 to 15 flower buds per stem. Development as a panicle.

Flower bloom:

*Fragrance*.—Moderate.

*Duration*.—The blooms have a duration on the plant of approximately 15 days. Petals fall cleanly away from plant after flowers have fully matured.

*Size*.—Flower diameter is 110 mm when open. Flower depth is 40 mm.

*Flower shape*.—High centered, double, with a high pointed center which is tightly closed. After flowers open more appearance as a rosette.

*Shape of flower, side view*.—The upper portion is convex, the lower portion is concave.

Petalage: Under normal conditions, flowers have about 35 petals.

General tonality of flower: Open flowers are Yellow Group 9B.

Petal color:

*Upon opening, outer petals*.—Upper surface: Base, Yellow Group 9A. Margins are Yellow Group 8B. Lower surface: Yellow Group 13C at margins. Basal to mid zone Yellow Group 13B. At point of attachment Yellow Group 9B.

*Upon opening, inner petals*.—Upper surface: Yellow Group 9A Lower surface: Yellow Group 11A at margins. Yellow 12B at middle and basal zone.

*Basal petal spots*.—No distinctive coloration at the base of the petal upon opening.

*After opening, outer petals*.—Upper surface: Yellow Group 4B at margins, Yellow Group 5B at mid and basal zone. Lower surface: Yellow Group 8B margins and middle zone. At basal zone Yellow Group 8A.

*After opening, inner petals*.—Upper surface: Yellow Group 4B at margins, Yellow Group 5B at mid and basal zone. Lower surface: Yellow Group 8B margins and middle zone. At basal zone Yellow Group 8A.

*Basal petal spots*.—No distinctive coloration at the base of the petal after opening.

Petals:

*Petal reflex*.—Slightly reflexed.

*Margin*.—Entire and uniform. Light undulations.

*Shape*.—Rounded. Apex shape: Rounded. Base shape: Rounded.

*Size*.—55 mm (l) 55×mm (w).

*Texture*.—Smooth.

*Thickness*.—Average.

Petaloids:

*Size*.—15 mm (l) by 13 mm (w).

*Quantity*.—About 4.

*Shape*.—Elliptical with an acute base and rounded apices.

*Color*.—Yellow Group 9A on the upper surface. At lower surface, Yellow Group 11A.

Reproductive flower parts:

*Pollen*.—None observed.

*Anthers*.—Size: 2 mm in length. Color: Yellow Group 11A. Quantity: 42 on average.

*Filaments*.—Color: Yellow Group 13A. Length: 7 mm.

*Pistils*.—Length: 4 mm. Quantity: 30 on average.

*Stigmas*.—Color: Yellow-White Group Greyed-Yellow Group 160A.

*Styles*.—Color: Greyed-Red Group 180D.

*Location of stigmas*.—Level in location relative to the length of the filaments and the height of the anthers.

*Hips*.—None Observed.

PLANT

Plant growth: Upright, well branched, and bushy.

Plants are about 100 to 115 cm in height, and 95 cm wide.

Stems:

*Color of juvenile growth*.—Yellow-Green Group 144B with intonations of Greyed-Orange Group 174A.

*Color of mature growth*.—Yellow-Green Group 144A.

*Length*.—Canes are about 45 cm from the base of the plant to the flowering portion.

*Diameter*.—About 8 mm.

*Internodes*.—On mature canes about 55 mm between nodes.

*Surface texture*.—Young wood: Smooth. Older wood: Smooth.

Long prickles: None observed.

Plant foliage:

*Compound leaf.*—150 mm (l)×125 (w).

*Quantity.*—2 leaves per 10 cm of stem on average.

*Leaf bearing angle to the stem.*—45 degrees.

*Color of juvenile foliage.*—Upper side: Greyed-Purple Group 187A. Lower side: Greyed-Red Group 183C.

*Color of mature foliage.*—Upper side: Yellow-Green Group 147A. Lower side: Yellow-Green Group 146B.

Plant leaves and leaflets:

*Stipules.*—Size: 29 mm long, 15 mm wide. Quantity: 2 per compound leaf. Shape: Linear, slightly broad based with outward extending apices. Margins: Finely serrated. Color: Yellow-Green Group 144A.

*Petiole.*—Length: 35 mm. Diameter: 2 mm. Upper surface color: Yellow-Green Group 144A with intonations of Greyed-Red Group 180A. Lower surface color: Yellow-Green Group 144A.

*Rachis.*—Length: 45 mm with diameter of about 2 mm. Upper surface color: Yellow-Green Group 144A with intonations of Greyed-Red Group 180A. Lower surface color: Yellow-Green Group 144A.

*Leaflet.*—Quantity: Normally 5 leaflets. Margins: Serrated. Size: Terminal leaflets are about 65 mm long, 50 mm wide. Shape: Generally round. Base: Rounded. Apex: Mucronate. Texture: Smooth. Thickness: Average. Arrangement: Odd pinnate. Venation: Reticulate. Glossiness: Very glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

Pest resistance: The variety exhibits above average resistance to the Western Flower Thrip *Frankliniella occidentalis*. Otherwise the variety is susceptible to insect pests normally associated with roses.

I claim:

1. A new and distinct variety of rose plant of the Floribunda rose class named 'Poulcas056', substantially as illustrated and described herein, due to its abundant yellow flowers, disease resistance, and extended period of bloom.

* * * * *

'Poulcas056'

'Poulcas056'

'Poulcas056'